| United States Patent [19] | [11] Patent Number: 4,983,450 |
| Yanagihara et al. | [45] Date of Patent: Jan. 8, 1991 |

[54] GAS-PERMEABLE, WATERPROOF NONWOVEN FABRIC AND PROCESS FOR ITS PRODUCTION

[75] Inventors: Takeshi Yanagihara; Tsugio Honda; Makoto Nakano; Hiroshi Kajino, all of Kanagawa, Japan

[73] Assignees: Mitsue Toatsu Chemicals, Inc., Tokyo; Uni-Charm Corporation, Kawanoe, both of Japan

[21] Appl. No.: 251,214

[22] PCT Filed: Nov. 17, 1987

[86] PCT. No.: JP87/00889

§ 371 Date: Jul. 28, 1988

§ 102(e) Date: Jul. 28, 1988

[87] PCT Pub. No.: WO88/03870

PCT Pub. Date: Jun. 2, 1988

[30] Foreign Application Priority Data

Nov. 18, 1986 [JP] Japan ................................ 61-276191

[51] Int. Cl.$^5$ ................................................ B32B 5/16
[52] U.S. Cl. ..................... 428/283; 427/245; 427/365; 427/389.9; 428/284; 428/286; 428/287; 428/323; 428/327
[58] Field of Search ............... 428/284, 286, 287, 289, 428/290, 283, 323, 327; 427/365, 389.9, 245

[56] References Cited

U.S. PATENT DOCUMENTS

| 4,438,167 | 3/1984 | Schwarz | 418/138 |
| 4,508,775 | 4/1985 | Adiletta | 418/188 |
| 4,684,568 | 8/1987 | Lou | 428/265 |

FOREIGN PATENT DOCUMENTS 1240586  7/1971  United Kingdom .

*Primary Examiner*—James J. Bell
*Attorney, Agent, or Firm*—Kane, Dalsimer, Sullivan, Kurucz, Levy, Eisele & Richard

[57] ABSTRACT

A porous waterproof nonwoven fabric having a superior gas-permeability and waterproofness, capable of being produced at cheap cost under simple processing conditions and by means of simple processing equipments, having superior mechanical strengths and a good feeling and useful for disposable uses and a process for producing the fabric are provided, which fabric comprises a thermoplastic resin composition film comprising a thermoplastic resin and a specified quantity of a filler, the thermoplastic resin composition film having fine pores formed by calender processing.

8 Claims, No Drawings

GAS-PERMEABLE, WATERPROOF NONWOVEN FABRIC AND PROCESS FOR ITS PRODUCTION

BACKGROUND OF THE INVENTION

1. Field of the Invention

This invention relates to a porous waterproof nonwoven fabric having both of gas-permeability and waterproofness and a process for producing the same.

2. Description of the Related Art

The prior art directed to porous waterproof nonwoven fabric has mostly been carried out mainly by subjecting a gas-permeable nonwoven fabric substrate to coating process with a resin to form a resin film on the substrate and thereby impart a superior waterproofness thereto. However, according to such a process, it has been difficult to impart a sufficient gas-permeability and the resulting product has been difficult to be regarded as a substantially gas-permeable waterproof nonwoven fabric, and further, dampness due to sweat and moisture excreted from the body at the time of its wearing has given a disagreeable feeling.

As a technique for solving this problem, a process referred to as wet coating process has been known. For example, Japanese patent application laid-open No. Sho 56-26076 discloses a process wherein a solution of an urethane polymer dissolved in a polar organic solvent is coated onto a substrate, followed by dripping the resulting material in a water bath to remove the polar solvent and thereby form a finely porous polyurethane film having a gas-permeability However, the process has drawbacks that the production steps are complicated and the allowable ranges of the production conditions are narrow.

According to the process, since a polyurethane resin which is an expensive raw material is used and particular processing conditions and processing equipments are required, the resulting film is so expensive that the resulting product can be used only for limited high-class clothes; hence the product has a drawback that it cannot be used for example for disposable uses or similar uses.

Further, gas-permeable waterproof nonwoven fabrics are required to have a good feeling in view of their uses; hence conventional products have also been insufficient in this aspect.

An object of the present invention is to provide a porous waterproof nonwoven fabric which is superior in both of the properties of gas-permeability and waterproofness.

Another object of the present invention is to provide a porous waterproof nonwoven fabric which can be produced under simple processing conditions and using simple processing equipments.

Still another object of the present invention is to provide a porous waterproof nonwoven fabric which can be produced at cheap cost and hence is suitable to disposable uses.

Further still another object of the present invention is to provide a porous waterproof nonwoven fabric having superior mechanical strengths.

Furthermore still another object of the present invention is to provide a porous waterproof nonwoven fabric having a superior feeling.

Still another object of the present invention is to provide a process for producing a porous waterproof nonwoven fabric having the above-mentioned properties.

SUMMARY OF THE INVENTION

In accordance with the present invention, there are provided a gas-permeable waterproof nonwoven fabric which comprises a thermoplastic resin composition film comprising 100 parts by weight of a thermoplastic resin and 1 to 50 parts by weight of a filler and a nonwoven fabric, the thermoplastic resin composition film having fine pores formed by calender processing; a process for producing a gas-permeable waterproof nonwoven fabric which comprises subjecting to calender processing, a thermoplastic resin composition film comprising 100 parts by weight of a thermoplastic resin and 1 to 50 parts by weight of a filler, followed by applying a nonwoven fabric onto the resulting film; a process for producing a gas-permeable waterproof nonwoven fabric which comprises applying a thermoplastic resin composition film comprising 100 parts by weight of a thermoplastic resin and 1 to 50 parts by weight of a filler onto a nonwoven fabric, followed by subjecting the resulting material to calender processing; and a process for producing a gas-permeable waterproof nonwoven fabric which comprises coating a nonwoven fabric with a thermoplastic resin composition comprising 100 parts by weight of a thermoplastic resin and 1 to 50 parts by weight of a filler, followed by subjecting the resulting material to calender processing.

DETAILED DESCRIPTION OF PREFERRED EMBODIMENTS

As the thermoplastic resin used in the present invention, those which match the nonwoven fabric in the aspect of its strengths, waterproofness, feeling, appearance, cost, etc. are used.

Concrete examples thereof are acrylic resins, urethane resins, synthetic rubbers, ethylene-vinyl acetate copolymer resins, etc.

Examples of acrylic resins are polymers of alkyl acrylates or alkyl methacrylates such as methyl acrylate, methyl methacrylate, ethyl acrylate, ethyl methacrylate, propyl acrylate, propyl methacrylate, butyl acrylate, butyl methacrylate, pentyl acrylate, pentyl methacrylate, hexyl acrylate, hexyl methacrylate, heptyl acrylate, heptyl methacrylate, octyl acrylate, octyl methacrylate, octadecyl acrylate, octadecyl methacrylate, etc. and copolymers of the foregoing esters with ethylenic unsaturated aromatic monomers such as styrene, $\alpha$-methylstyrene, vinyltoluene, etc., unsaturated nitriles such as acrylonitrile, methacrylonitrile, etc., vinyl esters such as vinyl acetate and vinyl propionate, ethylenic unsaturated carboxylic acids such as acrylic acid, methacrylic acid, itaconic acid, fumaric acid, maleic anhydride, crotonic acid, etc., hydroxyalkyl ethylenic unsaturated carboxylates such as 2-hydroxypropyl acrylate, 2-hydroxyethyl methacrylate, etc., glycidyl ethylenic unsaturated carboxylates such as glycidyl acrylate, glycidyl methacrylate, etc., and acrylamide, methacrylamide, N-methylol acrylamide, N-methylol methacrylamide, N-butoxymethyl acrylamide, diacetone acrylamide, etc.

Examples of urethane resins are polyester or polyether urethane elastomers prepared from polyesters or polyether diols and diisocyanates.

Polyesters referred to herein are those obtained by polycondensation of polycarboxylic acids with polyols.

Examples of the polycarboxylic acids referred to herein are aliphatic saturated dibasic acids such as malonic acid, succinic acid, glutanic acid, adipic acid, azelaic acid, sebacic acid, hexahydrophthalic anhydride, etc., aliphatic unsaturated dibasic acids such as maleic acid, maleic anhydride, fumaric acid, itaconic acid, citraconic acid, etc., aromatic dibasic acids such as phthalic anhydride, phthalic acid, terephthalic acid, isophthalic acid, etc., and lower alkyl esters of the foregoing.

Examples of the polyols referred to herein are diols such as ethylene glycol, 1,2-propylene glycol, 1,3-propylene glycol, 1,3-butylene glycol, 1,4-butylene glycol, 1,6-hexanediol, neopentyl glycol, diethylene glycol, dipropylene glycol, hydrogenated bisphenol A, adduct of bisphenol A to ethylene oxide, adduct of bisphenol A to propylene oxide, etc., and triols such as glycerine, trimethylolpropane, trimethylolethane, etc.

Examples of polyether diols are polyethylene glycol, polypropylene glycol, polytetramethylene glycol, polycaprolactone, etc., and these may also be used as polyols which are used in the preparation of polyesters.

Examples of diisocyanates to be reacted with the above polyesters or polyether diols are hexamethylene diisocyanate, isophorone diisocyanate, tolylene diisocyanate, diphenylmethane diisocyanate, xylene diisocyanate, tetramethylxylene diisocyanate, etc.

As the synthetic rubbers, copolymers of at least one of styrene, methyl methacrylate and acrylonitrile with butadiene may be used. If necessary, copolymers of the foregoing with a functional group monomer such as ethylenic unsaturated carboxylic acids such as acrylic acid methacrylic acid, itaconic acid, fumaric acid, maleic anhydride, crontonic acid, etc., hydroxyalkyl ethylenic unsaturated carboxylates such as 2-hydroxypropyl acrylate, 2-hydroxyethyl methacrylate, etc., glycidyl ethylenic unsaturated carboxylates such as glycydyl acrylate, glycidyl methacrylate, etc. and acrylamide, methacryl amide, N-methylol acrylamide, N-methylol methacrylamide, N-butoxymethyl acrylamide, diacetone acrylamide, etc.

The filler used in the present invention refers to inorganic or organic fine particles, and among these, organic fine particles are preferred. The form thereof is not always necessary to be spherical, but it may be hollow, flat, acicular or porous, that is, it has no particular limitation. Examples of inorganic fillers are glass beads, silica, calcium carbonate, barium sulfate, silica-alumina gel, pearlite, diatomaceous earth, zeolite, white carbon, etc. The organic fillers refer to fine particles of thermoplastic resins or thermoset resins. Examples thereof are fine particles of fluorine resins, silicone resins, polyethylene, polypropylene, ethylene-vinyl acetate resins, nylon, polyester resins, polyamide resins, polystyrene resin, acrylic resins, cellulose acetate, butyrate resins, urea resins, phenolic resins, epoxy resins, etc. Concrete examples of such fillers are U PEARL (urea resin; trademark of a product made by Mitsui Toatsu Chemicals, Inc.), BARINAX (polyester resin; trademark of a product made by Mitsui Toatsu Chemicals, Inc.), KPL (fluorine resin; trademark of a product made by Kitamura Company), FLO-THENE(-polyethylene resin; trademark of a product made by Seitetsu Kagaku Company), etc. The resins are not limited particularly to the above resins as far as fine particles can be made therefrom. The above fillers may be used alone or in adequate admixture.

In view of waterproofness, the filler itself is preferred to be water-repellent, and fluorine resins, silicone resins, polyethylene, polypropylene, etc. are more suitable.

The particular size of the filler is preferably in the range of 1 to 50 $\mu$m, more preferably 3 to 40 $\mu$m in terms of the average particle size. Further, it is preferred to have the same thickness as or larger than that of the resulting porous waterproofing film. The average particle size referred to herein means the size of a secondary particle regarded as one particle in the case where particles agglomerate. Further, as to the particle size, when the filler particle is spherical, it refers to the diameter of the spherical particle, while when the particle is non-spherical, it refers to a diameter calculated from that of a spherical body having the same volume as that of the non-spherical particle.

The quantity of the filler used in the present invention is in the range of 1 to 50 parts by weight, preferably 5 to 30 parts by weight based on 100 parts by weight of the thermoplastic resin. If the quantity is less than 1 part by weight, no sufficient airpermeability is obtained, while if it exceeds 50 parts by weight, it is difficult to retain the strength as the nonwoven fabric and also the resulting product is inferior in the waterproofness.

The reason of using a nonwoven fabric in the present invention is that it is possible to reduce the thickness of water-proofing fabric and also make it lightweight and further the resulting product has a superior feeling. Further, the product is cheap and hence suitable to disposable use applications. If other bases such as clothes, etc. are used, the resulting product is insufficient particularly in feeling and unsuitable to use applications such as diaper where the resulting product is contacted directly with skin.

The nonwoven fabric referred to in the present invention may be wet nonwoven fabric, spun-bonded nonwoven fabric, dry nonwoven fabric, stitch-bonded nonwoven fabric, needle-punched nonwoven fabric, spun rayon nonwoven fabric, hot-melt-adhesive nonwoven fabric, etc. and although it is not particularly limited to these, spun-bonded nonwoven fabric is preferred in that the fabric is superior in the gas-permeability and strength and also since no treatment with oiling agents participates in the production process, it is possible to make the best use of properties characteristic of used fibers.

Examples of fibers constituting such nonwoven fabrics are polyester fibers, nylon fibers, polyacrylic fibers, polyolefin fibers, rayon fibers, etc., and these fibers may be used alone or in admixture.

As to the form of the porous waterproof nonwoven fabric, the fabric may be a material obtained by arranging a nonwoven fabric on at least one surface of a thermoplastic resin composition film, and as to the form of the nonwoven fabric, the fabric may be a single nonwoven fabric or a material obtained by integrating a plurality of nonwoven fabrics composed of the same or different kinds of fiber layers in a conventional manner. For example, a sandwich type porous waterproof nonwoven fabric obtained by arranging a nonwoven fabric composed of hydrophilic fibers on one surface of a resin composition film and a nonwoven fabric composed of hydrophobic fibers on the other surface thereof may be suitable for uses as clothes, but a number of variations may be possible depending on the uses and objects thereof, and there is no particular limitation thereto.

The basis weight of the nonwoven fabric also has no particular limitation, but it is preferably in the range of 10 to 120 g/m². If it is less than 10 g/m², the resulting material does not constitute the form of nonwoven fabric.

As to the process for producing the porous waterproof nonwoven fabric of the present invention, the following representative processes may be considered:

A first process is carried out by forming a film composed of a thermoplastic resin composition containing a filler, followed by imparting gas-permeability thereto according to calender processing and then applying the resulting material onto a nonwoven fabric. A second process is carried out by forming a film composed of a thermoplastic resin composition containing a filler, applying the film onto a nonwoven fabric and then imparting gas-permeability to the resulting material according to calendering processing. A third process is carried out by directly coating a nonwoven fabric with a thermoplastic resin composition containing a filler and then subjecting the resulting material to calender processing to impart gas-permeability to the calendered material. In the aspect of steps, the third process is preferred in that an adhesion step is unnecessary, but even the second process has an advantage that the calender processing and the adhesion step can be simultaneously carried out. Further, the first and second processes are effective particularly in the case of a nonwoven fabric having a low basis weight and wide-meshes due to which no uniform coating can be obtained when the fabric is directly coated.

As to the process for forming a film in the first and second processes, it is necessary to choose an adequate film-making process depending on the characteristics of the thermoplastic resin. For example, as to acrylic resins, urethane resins, synthetic rubbers, etc., it has often been commercially employed to form a film in the form of a solution in solvent or in the form of an aqueous dispersion such as latex, emulsion, etc. according to coating process. At that time, if necessary, a curing agent may be contained therein in order to improve the coating strength of the thermoplastic resin and improving the water resistance thereof. Particularly when the thermoplastic resin has a functional group in the solvent solution or the aqueous dispersion, a curing agent is often used at the same time. As the curing agent, melamine resins, urea resins, epoxy resins, metal chelate compounds, isocyanate compounds, aziridine compounds, etc. may be used, if necessary.

If the case of coating process, for example, the solvent solution or aqueous emulsion of the thermoplastic resin may be applied directly onto a release paper or a release film by means of a coater such as knife coater, bar coater, roll coater, flow coater or the like, followed by drying the resulting material to form a coating and then stripping the resulting coating from the release paper or the release film to obtain the coating.

In the third process, coating is carried out directly onto a nonwoven fabric, but the coating may be carried out in the same manner as in the above process. It is possible to use a curing agent at the same times as in the above process.

The filler is necessary to choose also taking into account the above production process of the waterproof nonwoven fabric. For example, in the case where it is produced using a solvent solution, it is necessary to choose a filler insoluble in the solvent used. In the case where it is produced using an aqueous dispersion, it is necessary to choose a filler which is unchanged in the properties by water. As described above, an adequate filler varies depending on the state employed.

Imparting of the gas-permeability is carried out by calender processing. Namely, an external force is applied onto a thermoplastic resin composition film having a filler mixed with and dispersed in a thermoplastic resin according to calender processing to form clearances between the filler and the thermoplastic resin film and also break the surface of the continued film, whereby continued fine pores are prepared to obtain the gas-permeability.

As to the gas-permeability, usually the higher the linear pressure of calender and the larger the number of times of calendering, the easier the imparting of the gas-permeability. Thus, the control of the gas-permeability required may be easily effected by choosing the film thickness, the kind, average particle diameter and added quantity of the filler, calender conditions, etc. Usually, the calender temperature is preferably in the range of 0° to 150° C., more preferably 15° to 100° C. and the linear pressure is preferably in the range of 1 to 200 kg/cm, more preferably 10 to 100 kg/cm. The calender velocity is preferably in the range of 5 to 200 m/min., more preferably 30 to 100 m/min. Further, the number of times of the calendering has no particular limitation, but usually it is in the range of once to 10 times.

The diameter of the gas-permeable holes of the thus processed porous waterproof nonwoven fabric is preferably in the range of 0.1 to 10 $\mu$m, more preferably 0.5 to 5 $\mu$m, and such a range is practically suitable since the gas-permeability and the waterproofness are well balanced in the range.

The control of the diameter of the gas-permeable holes may be carried out by adequately choosing the film thickness, the kind, average particle diameter and added quantity of the filler, calender conditions, etc. as described above.

Further, in order to improve the waterproofness and water-repellency, water-repelling treatment may be carried out after the calender processing, if necessary. The water-repelling treatment may be carried out according to impregnation process, patting process, coating process, etc., using an aqueous dispersion of e.g. fluorine repellant, silicone repellant, etc., followed by drying and heat treatment to thereby obtain a water-repellent effect.

The present invention will be described in more detail by way of Examples, but it should not be construed to be limited thereto.

EXAMPLE 1

As the resin used in this Example, the following resin was produced and used as a sample for the subsequent tests:

Distilled water (150 parts by weight), potassium persulfate (0.5 part by weight), sodium dodecylbenzene sulfonate (1.0 part by weight) and acrylamide (3 parts by weight) were fed in a flask, followed by raising the temperature up to 70° C. under $N_2$ purging, thereafter continuously dropwise adding butyl acrylate (66 parts by weight), acrylonitrile (23 parts by weight), acrylic acid (4 parts by weight) and hydroxyethyl methacrylate (4 parts by weight) to complete polymerization and thereby obtain an acrylic emulsion having a solids content of 40%.

A mixture consisting of the above-mentioned acrylic emulsion of butyl acrylate, etc. (solids content: 40%)

(250 parts by weight),FLO-THENE(tradename of product made by Seitetsu Kagaku Company; average particle diameter, 25 μm) as a polyethylene filler (10 parts by weight) and a defoamer (1.0 part by weight) was dispersed by means of a disperser, followed by thickening the dispersion with aqueous ammonia up to 5,000 cp (BM type viscometer, 60 rpm), applying the resulting material onto a silicone-treated release paper by means of Comma Bar Coater (tradename of an instrument made by Hirano Kinzoku Company) so as to give a dry film thickness of 15 μm, drying the resulting material at 100° C., curing it at 130° C. for 2 minutes, placing a spun-bonded nonwoven fabric of a polyester having a short fiber denier of 0.02 and a basis weight of 20 g/m² on the release paper having the thermoplastic resin composition containing the filler coated thereonto, applying the latter onto the former by means of Mini Calender Roll (tradename of a roll made by Yuri Roll Machine Company) and also subjecting these to calender processing (temperature: 20° C.; linear pressure: 20 kg/cm, and velocity: 10 m/min.) and stripping off the release paper to obtain a porous waterproof nonwoven fabric.

EXAMPLES 2 TO 5

Example 1 was repeated except that the kind and quantity of the filler were varied as indicated in Table 1 to obtain porous waterproof nonwoven fabrics.

COMPARATIVE EXAMPLE 1

For comparison with the present invention, a material having removed the filler from the mixture of Example 1 was processed in the same manner as in Example 1 to obtain a waterproof nonwoven fabric.

These results are shown in Table 1.

TABLE 1

|  | Example 1 | Example 2 | Example 3 | Example 4 | Example 5 | Compar. ex. 1 |
|---|---|---|---|---|---|---|
| Organic filler | Polyethylene | Fluorine resin | Urea resin | Silicone resin | Polyester resin | None |
| Average particle size (μm) | 15 | 25 | 10 | 20 | 25 | — |
| Acrylic emulsion/ organic filler | 100/15 | 100/15 | 100/20 | 100/15 | 100/20 | — |
| Calender processing | Twice | Twice | Three times | Twice | Three times | Twice |
| Gas-permeability (sec/100 cc) | 550 | 310 | 1320 | 410 | 1550 | 5000 or more |
| Water-resistant pressure (mmH$_2$O) | 1000 | 1100 | 750 | 1050 | 850 | 1400 |

*The ratio of acrylic emulsion to organic filler is expressed in terms of a ratio of solids contents.

EXAMPLES 6 TO 9

As the resins used in these Examples, the following resins were prepared and used as samples for the subsequent tests:

Distilled water (100 parts by weight), potassium persulfate (0.8 part by weight), sodium dodecylsulfate (1.5 part by weight) and itaconic acid (1.0 part by weight) were introduced into an autoclave, followed by raising the temperature up to 60° C. under N$_2$ purge. thereafter continuously dropwise adding styrene (47 parts by weight), butadiene (50 parts by weight) and hydroxyethyl acrylate (2 parts by weight) to complete polymerization, neutralizing the resulting SBR latex with ammonia, and further deodorizing it by steam stripping to obtain a SBR latex having a solids content of 50%.

This resin and polyethylene or fluorine resin each as a filler were used and the content of these fillers were varied, and applying and processing were carried out in the same manner as in Example 1 to obtain porous waterproof nonwoven fabrics. These results are shown in Table 2.

Further, for comparison with the present invention, the ratio of SBR latex to polyethylene or fluorine resin filler was changed to 100/60 (Comparative examples 2 and 3).

TABLE 2

|  | Filler | Particle size (μm) | SBR/ Organic filler | Calender processing | Gas-permeability (sec/100 cc) | Water-resistant pressure (mmH$_2$O) |
|---|---|---|---|---|---|---|
| Example 6 | Polyethylene | 15 | 100/5 | Twice | 1200 | 1200 |
| Example 7 | Polyethylene | 15 | 100/30 | Twice | 380 | 850 |
| Example 8 | Fluorine resin | 25 | 100/5 | Twice | 720 | 1050 |
| Example 9 | Fluorine resin | 25 | 100/30 | Twice | 210 | 900 |
| Compar. ex. 1 | None | — | 100/0 | Twice | 5000 or more | 1400 |

TABLE 2-continued

|  | Filler | Particle size (μm) | SBR/ Organic filler | Calender processing | Gas-per-meability (sec/100 cc) | Water-resistant pressure (mmH₂O) |
|---|---|---|---|---|---|---|
| Compar. ex. 2 | Polyethylene | 15 | 100/60 | Twice | 170 | 250 |
| Compar. ex. 3 | Fluorine resin | 25 | 100/60 | Twice | 120 | 300 |

*The ratio of SBR latex to organic filler is expressed in terms of the ratio of solids contents.

EXAMPLES 10 TO 14

The acrylic emulsion of butyl acrylate, etc. (solids content: 40%) used in Example 1 was used as a thermoplastic resin, and polyethylene or a silicone resin, each having the average particle diameter varied, was used as a filler, and applying and processing were carried out in the same manner as in Example 1, but varying the thickness of coating to obtain porous waterproof nonwoven fabrics. These results are shown in Table 3.

In addition, the ratio of the acrylic emulsion to the organic filler was set to 100/15.

TABLE 3

|  | Filler | Particle size (μm) | Dry film thickness (μm) | Frequency of calendering | Gas-permeability (sec/100 cc) | Water-resistant pressure (mmH₂O) |
|---|---|---|---|---|---|---|
| Example 10 | Polyethylene | 3 | 15 | Twice | 1310 | 1400 |
| Example 11 | Polyethylene | 40 | 20 | Twice | 480 | 650 |
| Example 12 | Silicone resin | 35 | 20 | Twice | 550 | 750 |
| Example 13 | Polyethylene | 0.5 | 15 | Twice | 4600 | 1400 |
| Example 14 | Polyethylene | 60 | 30 | Twice | 290 | 550 |

EXAMPLES 15 TO 18

Polyethylene (average particle size: 15μ) was used as a filler and various kinds of nonwoven fabrics indicated in Table 4 were used each as a base, and applying and processing were carried out in the same manner as in Example 1 to obtain composite porous waterproof nonwoven fabrics.

COMPARATIVE EXAMPLE 4

Example 18 was repeated except that the nonwoven fabric was replaced by a nylon taffeta (112 warp yarns/inch and 97 weft yarns/inch) to obtain a composite porous waterproof cloth.

COMPARATIVE EXAMPLE 5

Example 4 was repeated except that the nonwoven fabric was replaced by a sized paper obtained by subjecting a paper of 100% pulp to post-processing with a wax sizing agent and having a basis weight of 25 g/m², to obtain a composite porous waterproof paper.

COMPARATIVE EXAMPLE 6

For comparison with the present invention, the thermoplastic resin film in advance of being applied onto the nonwoven fabric obtained in Example 1 and not subjected to calender processing was stripped from the release paper, followed by applying it onto the nonwoven fabric, to measure the gas-permeability and water-resistant pressure. These results are shown in Table 4.

TABLE 4

|  | Example 15 | Example 16 | Example 17 | Example 18 | Compar. ex. 4 | Compar. ex. 5 | Compar. ex. 6 |
|---|---|---|---|---|---|---|---|
| Substrate | Nonwoven fabric | Nonwoven fabric | Nonwoven fabric | Nonwoven fabric | Nylon taffeta | Sized paper | Nonwoven fabric |
| Denier | 0.02 | 0.02 | 0.2 | 0.08 |  |  | 0.02 |
| Basis weight (g/m²) | 20 | 20 | 40 | 45 |  | 25 | 20 |
| Stock | Polyester | Polyester | Polyester | Nylon |  |  | Polyester |
| Acrylic emulsion/ Polyethylene | 100/15 | 100/15 | 100/15 | 100/15 | 100/15 | 100/15 | 100/15 |

TABLE 4-continued

|  | Example 15 | Example 16 | Example 17 | Example 18 | Compar. ex. 4 | Compar. ex. 5 | Compar. ex. 6 |
|---|---|---|---|---|---|---|---|
| Frequency of calendering | 3 times | 4 times | Twice | Twice | Twice | Twice | 0 |
| Gas-permeability (sec/100 cc) | 430 | 320 | 560 | 400 | 470 | 980 | 5000 or more |
| Water-resistant pressure (mmH₂O) | 850 | 650 | 900 | 1100 | 800 | 1100 | 1400 |
| Feeling |  | Δ |  |  | X | X |  |

As to the measurement of the feeling, evaluation was carried out according to a feeling test by hand.
: very soft feeling
: soft feeling
Δ: somewhat stiff feeling
X: stiff feeling

EXAMPLE 19

The acrylic emulsion of butylacrylate, etc. containing polyethylene filler used in Example 1 was applied directly onto the nonwoven fabric used in Example 20 by means of a roll over knife coater so as to give a dry film thickness of 15μ, followed by drying the resulting material and subjecting it to processing under the same calender conditions as in Example 1 to obtain a porous waterproof nonwoven fabric.

This porous nonwoven fabric had a gas-permeability of 380 seconds/100 cc, a water-resistant pressure of 800 mmH₂O and a very soft feeling.

The porous waterproof nonwoven fabric provided according to the present invention is usable for clothes, waterproof covers, hygienic materials such as diaper, garments such as surgical gown, rain coat, etc. and also usable for disposable uses.

What we claim is:

1. A gas-permeable, waterproof nonwoven fabric which comprises a thermoplastic resin composition film comprising 100 parts by weight of a thermoplastic resin and 1 to 50 parts by weight of a filler, said filler being fine particles of an organic resin filler having the particle size of 1 to 50 microns selected from the group consisting of thermoplastic resins and thermosetting resins, and a nonwoven fabric, said thermoplastic resin composition film having fine pores formed by calendar processing.

2. A gas-permeable nonwoven fabric according to claim 1 wherein said thermoplastic resin is at least one member selected from the group consisting of acrylic resins, urethane resins, synthetic rubbers, ethylene-vinyl acetate copolymer resins one polyethylene resins.

3. A gas-permeable waterproof nonwoven fabric according to claim 1 wherein said filler is at least one member selected from the group consisting of fluorine resins, silicone resins, polyethylene and polypropylene.

4. A gas-permeable waterproof nonwoven fabric according to claim 1 wherein said nonwoven fabric is at least one member selected from the consisting of wet nonwoven fabric, spun-bonded nonwoven fabric, dry nonwoven fabric, stitch-bonded nonwoven fabric, needle-punched nonwoven fabric, spun rayon nonwoven fabric and hot-melt-adhesive nonwoven fabric.

5. A gas-permeable waterproof nonwoven fabric according to claim 1 wherein fibers constituting said nonwoven fabric are polyester fibers, nylon fibers, polyacrylic fibers, polyolefin fibers or rayon fibers, these fibers being used singly or in admixture.

6. A process for producing a gas-permeable waterproof nonwoven fabric, which process comprises subjecting to calender processing, a thermoplastic resin composition film comprising 100 parts by weight of a thermoplastic resin and 1 to 50 parts by weight of a filler, said filler being fine particles of an organic resin filler having the particle size of 1 to 50 microns selected from the group consisting of thermoplastic resins and thermosetting resins, followed by applying a nonwoven fabric onto the resulting film.

7. A process for producing a gas-permeable waterproof nonwoven fabric, which process comprises applying a thermoplastic resin composition film comprising 100 parts by weight of a thermoplastic resin and 1 to 50 parts by weight of a filler onto a nonwoven fabric, said filler being fine particles of an organic resin filler having the particle size of 1 to 50 microns selected from the group consisting of thermoplastic resins and thermosetting resins, followed by subjecting the resulting material to calender processing.

8. A process for producing a gas-permeable waterproof nonwoven fabric, which process comprises coating a nonwoven fabric with a thermoplastic resin composition film comprising 00 parts by weight of a thermoplastic resin and 1 to 50 parts by weight of a filler, said filler being fine particles of an organic resin filler having the particle size of 1 to 50 microns selected from the group consisting of thermoplastic resins and thermosetting resins, followed by subjecting the resulting material to calender processing.

* * * * *

UNITED STATES PATENT AND TRADEMARK OFFICE
CERTIFICATE OF CORRECTION

PATENT NO. : 4,983,450

DATED : January 8, 1991

INVENTOR(S) : Takeshi Yanagihara; Tsugio Honda; Makoto Nakano; Hiroshi Kajino

It is certified that error appears in the above-identified patent and that said Letters Patent is hereby corrected as shown below:

Cover Page, Item [73], delete "Mitsue" and
substitute therefor --Mitsui--.

Signed and Sealed this

Sixteenth Day of November, 1993

Attest:

BRUCE LEHMAN

Attesting Officer

Commissioner of Patents and Trademarks